(12) United States Patent
Morriss et al.

(10) Patent No.: US 9,700,326 B2
(45) Date of Patent: Jul. 11, 2017

(54) SHAPEABLE GUIDE CATHETERS AND RELATED METHODS

(71) Applicant: Acclarent, Inc., Menlo Park, CA (US)

(72) Inventors: John H. Morriss, San Francisco, CA (US); Mei Pader, Humble, TX (US)

(73) Assignee: Acclarent, Inc., Irvine, CA (US)

( * ) Notice: Subject to any disclaimer, the term of this patent is extended or adjusted under 35 U.S.C. 154(b) by 58 days.

(21) Appl. No.: 14/265,888

(22) Filed: Apr. 30, 2014

(65) Prior Publication Data

US 2014/0330074 A1 Nov. 6, 2014

Related U.S. Application Data

(63) Continuation of application No. 11/804,309, filed on May 16, 2007, now Pat. No. 8,932,276, which is a (Continued)

(51) Int. Cl.
*A61M 25/00* (2006.01)
*A61B 17/16* (2006.01)
(Continued)

(52) U.S. Cl.
CPC .......... *A61B 17/1657* (2013.01); *A61B 17/24* (2013.01); *A61B 17/32002* (2013.01);
(Continued)

(58) Field of Classification Search
CPC ................ A61B 17/24; A61B 17/8866; A61B 2017/003; A61B 2017/3486;
(Continued)

(56) References Cited

U.S. PATENT DOCUMENTS

| 3,800,788 A | * | 4/1974 | White | ................ A61B 17/24 606/192 |
| 4,592,357 A | | 6/1986 | Ersek | |

(Continued)

FOREIGN PATENT DOCUMENTS

| JP | 10-034376 | 2/1989 |
| JP | 06-17751 | 3/1994 |

(Continued)

OTHER PUBLICATIONS

European Communication dated Sep. 27, 2011 for Application No. EP 06800540.4.

(Continued)

*Primary Examiner* — Kevin C Sirmons
*Assistant Examiner* — Deanna K Hall
(74) *Attorney, Agent, or Firm* — Frost Brown Todd LLC

(57) ABSTRACT

Shapeable guide catheters and methods for manufacturing and using such shapeable guide catheters. In one embodiment, the shapeable guide catheter comprises a tubular member having a shapeable region, a malleable shaping member attached to the shapeable region such that, when the shape of the shapeable region is changed from a first shape to a second shape, the shaping member will plastically deform to thereafter substantially hold the shapeable region in the second shape, a tubular outer jacket disposed about the outer surface of the tubular member and a tubular inner jacket disposed within the lumen of the tubular member. The shapeable region of the guide catheter may be manually formed into a desired shape before insertion of the guide catheter into the body. In some embodiments, the guide catheter is sized to be inserted through a nostril of a human patient and used to guide the transnasal insertion of another device (e.g., a guidewire, catheter, etc.) to a desired location within the nose, throat, ear or cranium of the subject.

10 Claims, 7 Drawing Sheets

Related U.S. Application Data continuation-in-part of application No. 11/150,847, filed on Jun. 10, 2005, now Pat. No. 7,803,150, which is a continuation-in-part of application No. 11/037,548, filed on Jan. 18, 2005, now Pat. No. 7,462,175, which is a continuation-in-part of application No. 10/944,270, filed on Sep. 17, 2004, now abandoned, which is a continuation-in-part of application No. 10/912,578, filed on Aug. 4, 2004, now Pat. No. 7,361,168, which is a continuation-in-part of application No. 10/829,917, filed on Apr. 21, 2004, now Pat. No. 7,654,997.

(51) Int. Cl.

| | |
|---|---|
| *A61B 17/88* | (2006.01) |
| *A61B 17/24* | (2006.01) |
| *A61B 17/32* | (2006.01) |
| *A61B 17/3207* | (2006.01) |
| *A61M 25/06* | (2006.01) |
| *A61M 25/10* | (2013.01) |
| *A61B 90/16* | (2016.01) |
| *A61B 34/20* | (2016.01) |
| *A61B 10/06* | (2006.01) |
| *A61B 17/34* | (2006.01) |
| *A61B 17/00* | (2006.01) |
| *A61B 18/00* | (2006.01) |
| *A61B 90/00* | (2016.01) |

(52) U.S. Cl.
CPC .... *A61B 17/32075* (2013.01); *A61B 17/8866* (2013.01); *A61B 34/20* (2016.02); *A61B 90/16* (2016.02); *A61M 25/0012* (2013.01); *A61M 25/0041* (2013.01); *A61M 25/0662* (2013.01); *A61M 25/10* (2013.01); *A61B 10/06* (2013.01); *A61B 17/3478* (2013.01); *A61B 90/361* (2016.02); *A61B 2017/003* (2013.01); *A61B 2017/00526* (2013.01); *A61B 2017/00946* (2013.01); *A61B 2017/320004* (2013.01); *A61B 2017/3486* (2013.01); *A61B 2017/3488* (2013.01); *A61B 2018/00392* (2013.01); *A61B 2034/2051* (2016.02); *A61M 25/007* (2013.01); *A61M 25/0053* (2013.01); *A61M 25/0054* (2013.01); *A61M 2025/105* (2013.01); *A61M 2025/1052* (2013.01)

(58) Field of Classification Search
CPC ............ A61F 11/002; A61M 25/0041; A61M 25/0662; A61M 25/10
See application file for complete search history.

(56) References Cited

U.S. PATENT DOCUMENTS

| | | | |
|---|---|---|---|
| 4,641,654 A | 2/1987 | Samson et al. | |
| 4,682,607 A | 7/1987 | Vaillancourt et al. | |
| 4,696,544 A | 9/1987 | Costella | |
| 4,784,117 A | 11/1988 | Miyazaki | |
| 4,953,553 A | 9/1990 | Tremulis | |
| 5,040,548 A | 8/1991 | Yock | |
| 5,099,845 A | 3/1992 | Besz et al. | |
| 5,195,971 A | 3/1993 | Sirhan | |
| 5,213,576 A | 5/1993 | Abiuso et al. | |
| 5,306,272 A | 4/1994 | Cohen et al. | |
| 5,370,640 A | 12/1994 | Koloff | |
| 5,385,562 A | 1/1995 | Adams et al. | |
| 5,386,828 A | 2/1995 | Owens et al. | |
| 5,395,367 A | 3/1995 | Wilk | |
| 5,752,971 A | 5/1998 | Rosenbluth et al. | |
| 5,820,592 A | 10/1998 | Hammerslag | |
| 5,826,576 A | 10/1998 | West | |
| 5,836,951 A | 11/1998 | Rosenbluth et al. | |
| 5,882,333 A | 3/1999 | Schaer et al. | |
| 5,967,984 A | 10/1999 | Chu et al. | |
| 5,976,074 A | 11/1999 | Moriyama | |
| 5,987,344 A | 11/1999 | West | |
| 6,063,022 A | 5/2000 | Ben-Haim | |
| 6,179,776 B1 | 1/2001 | Adams et al. | |
| 6,283,908 B1 | 8/2001 | Aviram et al. | |
| 6,304,768 B1 | 10/2001 | Blume et al. | |
| 6,328,730 B1 | 12/2001 | Harkrider, Jr. | |
| 6,379,319 B1 | 4/2002 | Garibotto et al. | |
| 6,381,485 B1 | 4/2002 | Hunter et al. | |
| 6,511,471 B2 | 1/2003 | Rosenman et al. | |
| 6,520,954 B2 | 2/2003 | Ouchi | |
| 6,562,022 B2 | 5/2003 | Hoste et al. | |
| 6,679,833 B2 | 1/2004 | Smith et al. | |
| 6,758,857 B2 | 7/2004 | Cioanta et al. | |
| 6,849,062 B2 | 2/2005 | Kantor | |
| 6,989,024 B2 | 1/2006 | Hebert et al. | |
| 7,048,711 B2 | 5/2006 | Rosenman et al. | |
| 7,056,314 B1 | 6/2006 | Florio et al. | |
| 7,117,039 B2 | 10/2006 | Manning et al. | |
| 7,131,969 B1* | 11/2006 | Hovda | A61B 18/1402 128/898 |
| 7,566,300 B2 | 7/2009 | Devierre et al. | |
| 7,697,972 B2 | 4/2010 | Verard et al. | |
| 7,720,521 B2* | 5/2010 | Chang | A61B 5/06 600/199 |
| 7,857,750 B2 | 12/2010 | Belafsky | |
| 7,927,271 B2 | 4/2011 | Dimitriou et al. | |
| 8,075,476 B2 | 12/2011 | Vargas | |
| 8,475,360 B2 | 7/2013 | Brown | |
| 8,529,439 B2 | 9/2013 | Ito et al. | |
| 8,715,169 B2 | 5/2014 | Chang et al. | |
| 8,721,591 B2 | 5/2014 | Chang et al. | |
| 8,747,389 B2 | 6/2014 | Goldfarb et al. | |
| 8,764,709 B2 | 7/2014 | Chang et al. | |
| 8,764,726 B2 | 7/2014 | Chang et al. | |
| 8,764,729 B2 | 7/2014 | Muni et al. | |
| 8,828,041 B2 | 9/2014 | Chang et al. | |
| 2002/0068851 A1 | 6/2002 | Gravenstein et al. | |
| 2005/0038319 A1 | 2/2005 | Goldwasser et al. | |
| 2005/0059931 A1* | 3/2005 | Garrison | A61M 25/10 604/101.04 |
| 2005/0228224 A1 | 10/2005 | Okada et al. | |
| 2010/0211007 A1 | 8/2010 | Lesch, Jr. et al. | |

FOREIGN PATENT DOCUMENTS

| | | |
|---|---|---|
| JP | 2000-126303 | 5/2000 |
| JP | 2004-049583 | 2/2004 |
| JP | 2005-323702 | 11/2005 |
| RU | 2108764 | 4/1998 |
| WO | WO 00/67834 | 11/2000 |
| WO | WO 01/68178 | 9/2001 |
| WO | WO 2007/034203 | 3/2007 |

OTHER PUBLICATIONS

U.S. Appl. No. 14/221,550, filed Mar. 21, 2014.
U.S. Appl. No. 14/221,621, filed Mar. 21, 2014.
U.S. Appl. No. 14/221,714, filed Mar. 21, 2014.
U.S. Appl. No. 14/265,787, filed Apr. 30, 2014.
U.S. Appl. No. 14/266,002, filed Apr. 30, 2014.
U.S. Appl. No. 14/266,025, filed Apr. 30, 2014.
U.S. Appl. No. 14/327,593, filed Jul. 10, 2014.
U.S. Appl. No. 14/464,948, filed Aug. 21, 2014.

* cited by examiner

SHAPEABLE GUIDE CATHETERS AND RELATED METHODS

RELATED APPLICATIONS

This application is a continuation of U.S. patent application Ser. No. 11/804,309, entitled "Shapeable Guide Catheters and Related Methods," filed May 16, 2007, now U.S. Pat. No. 8,932,276, which is a continuation in part of 1) U.S. patent application Ser. No. 11/037,548, entitled "Devices, Systems and Methods for Treating Disorders of the Ear, Nose and Throat," filed Jan. 18, 2005, now U.S. Pat. No. 7,462,175, which is a continuation in part of U.S. patent application Ser. No. 10/829,917, entitled "Devices, Systems and Methods for Diagnosing and Treating Sinusitis and Other Disorders of the Ears, Nose and/or Throat," filed on Apr. 21, 2004, now U.S. Pat. No. 7,654,997; 2) U.S. patent application Ser. No. 10/912,578, entitled "Implantable Device and Methods for Delivering Drugs and Other Substances to Treat Sinusitis and Other Disorders," filed on Aug. 4, 2004, now U.S. Pat. No. 7,361,168, which is a continuation in part of U.S. patent application Ser. No. 10/829,917, entitled "Devices, Systems and Methods for Diagnosing and Treating Sinusitis and Other Disorders of the Ears, Nose and/or Throat," filed on Apr. 21, 2004, now U.S. Pat. No. 7,654,997; 3) U.S. patent application Ser. No. 10/944,270, entitled "Apparatus and Methods for Dilating and Modifying Ostia of Paranasal Sinuses and Other Intranasal or Paranasal Structures," filed on Sep. 17, 2004, published as U.S. Pub. No. 2006/0004323 on Jan. 5, 2006, now abandoned, which is a continuation in part of U.S. patent application Ser. No. 10/829,917, entitled "Devices, Systems and Methods for Diagnosing and Treating Sinusitis and Other Disorders of the Ears, Nose and/or Throat," filed on Apr. 21, 2004, now U.S. Pat. No. 7,654,997, and 4) U.S. patent application Ser. No. 11/150,847, entitled "Devices, Systems and Methods Useable for Treating Sinusitis," filed Jun. 10, 2005, now U.S. Pat. No. 7,803,150, which is a continuation in part of U.S. patent application Ser. No. 10/944,270, entitled "Apparatus and Methods for Dilating and Modifying Ostia of Paranasal Sinuses and Other Intranasal or Paranasal Structures," filed on Sep. 17, 2004, now U.S. Pub. No. 2006/0004323, published on Jan. 5, 2006, now abandoned, which is a continuation-in-part of U.S. patent application Ser. No. 10/829,917, entitled "Devices, Systems and Methods for Diagnosing and Treating Sinusitis and Other Disorders of the Ears, Nose and/or Throat," filed on Apr. 21, 2004, now U.S. Pat. No. 7,654,997, the entire disclosure of each such earlier-filed application being expressly incorporated herein by reference.

FIELD OF THE INVENTION

The present invention relates generally to medical apparatus and methods and more particularly to guide catheters that can be pre-shaped prior to insertion into a patient's body and their methods of manufacture and use.

BACKGROUND OF THE INVENTION

Various shapeable catheters have been known in the prior art. In some instances, a malleable element (e.g., a stylet or wire) is inserted into the lumen of a flexible catheter. The malleable element is either pre-shaped prior to insertion, or it is bent to a desired shape after it has been inserted into the catheter. In either event, the malleable element imparts a desired shape to the flexible catheter. In either instances, all or part of the catheter is formed of a malleable material that can be plastically deformed to a desired shape prior to or after insertion into a patient's body.

For example, U.S. Pat. No. 4,834,709 (Banning, et al.) describes a catheter and stylet assembly which includes a silicone rubber catheter and a malleable stylet. The stylet is formed of malleable metal covered by a plastic cover. The stylet is inserted into the catheter to permit the catheter to be manually shaped into a desired form before insertion into the patient. The stylet is removable from the catheter after the catheter has been inserted into the patient's body.

U.S. Pat. No. 5,720,719 (Edwards, et al.) describes an ablative catheter having a conshapeable body. The catheter's conshapeable body includes a malleable tube and a flexible tube that allow the catheter to conform to the curvature of a cavity inside a patient's body.

U.S. Pat. No. 5,749,357 (Linder) describes a malleable introducer tube that is useable to an endotracheal tube or the like. The introducer incorporates a malleable and shape-retaining tube along at least a portion of its length. In one embodiment, intermediation of the length between the sheath and the clamp is made almost entirely by a malleable tube made of a ductile metal such as aluminum. The tube may be thick-walled to reduce the volume necessary to inflate the sheath. In another embodiment, only the introducer tip may be of a malleable metal, such as copper. Significant advantages are offered by the use and inclusion of resilient, malleable portions in the introducer.

U.S. Pat. No. 5,882,346 describes a shapeable catheter and method for positioning such shapeable catheter within a body cavity. A core wire which includes a pre-shaped region is slidably received within a lumen of the catheter. The catheter includes a rigid proximal section and a flexible distal section. During use, the distal end of the catheter is inserted into a patient's vasculature and is passed into a body cavity. The pre-shaped region of the core wire is then passed into the lumen and is straightened by the rigid proximal section of the catheter. As the core wire is advanced into the more flexible distal region of the catheter, it re-assumes its predetermined shape and causes the core wire to form the distal section of the catheter into the predetermined shape. The distal section of the catheter is positioned in contact with tissue in the body cavity, and electrodes carried by the distal end are used to map and/or ablate the tissue.

U.S. Pat. No. 5,993,462 (Pomeranz, et al.) describes a shapeable catheter wherein a core wire is pre-shaped and slidably received within a lumen of the catheter. The catheter includes a rigid proximal section and a flexible distal section. A pull wire may additionally be provided to allow the user to cause deflection at a distal portion of the catheter.

U.S. Pat. No. 6,280,433 describes a tubular introducer or guide catheter for directing an implantable medical device such as a lead or catheter to a desired location within a patient's body. In one embodiment of the invention, the introducer comprises a two-lumen tube. A first lumen is configured to receive the implantable medical device that is to be introduced. A second lumen is provided to receive an insertable, elongated guiding member such as a stylet, which may be shapeable in various orientations, and which may be used to alter the configuration of the introducer. The second lumen may be provided with an internal coil or other tubular reinforcement member to prevent perforation of this lumen by the guiding member when the introducer is in the patient's body.

U.S. Pat. No. 6,979,979 (Lawrence, et al.) describes a malleable cannula. A reinforcement member extends along a lumen of the cannula, such reinforcement member having an interior side facing the lumen and an exterior side facing away from the lumen. A malleable member extends along a portion of the exterior side of the reinforcement member. The malleable member may be constructed of a tube with a wire slidably received within the tube and may include an anchor.

U.S. patent application Ser. No. 11/037,548, now U.S. Pat. No. 7,462,175, issued on Dec. 9, 2008, of which this is a continuation-in-part, describes malleable guide catheters that are useable to facilitate transnasal insertion of other devices (e.g., guidewires, balloon catheters, lavage catheters, etc.) into paranasal sinuses or other locations within the ear, nose or throat of a patient. Additionally, a system of transnasal guide catheters having malleable proximal shafts and pre-set distal curves of 0°, 30°, 70°, 90° and 110° are available commercially (Relieva® Sinus Guide Catheters, Acclarent, Inc., Menlo Park, Calif.).

There remains a need for further development of new guide catheters that may be pre-shaped prior to insertion into a patient's body and their methods of manufacture and use for transnasal and/or other applications.

SUMMARY OF THE INVENTION

In accordance with the present invention, there is provided a shapeable guide catheter device comprising a tubular member having (a) a shapeable region, (b) a malleable shaping member attached to the shapeable region such that, when the shape of the shapeable region is changed from a first shape to a second shape, the shaping member will plastically deform to and will thereafter substantially hold the shapeable region in such second shape, (c) a tubular outer jacket disposed about the outer surface of the tubular member and (d) a tubular inner jacket disposed within the lumen of the tubular member. In some embodiments the shapeable region may be created by forming one or more cut(s), groove(s), aperture(s) in, or otherwise weakening, a discrete region of the wall of the tubular member, thereby rendering that region more flexible than the remainder of the tubular member and thus defining the shapeable region of the device.

Further in accordance with the present invention, there is provided a method for positioning a device at a desired location within the ear, nose, throat or cranium of a human or animal subject, such method generally comprising the steps of (A) providing a shapeable guide catheter having a distal end, a lumen and a shapeable region that shapeable to a desired shape such that it will thereafter substantially retain that desired shape, (B) forming the shapeable region to a desired shape, (C) inserting the guide catheter, distal end first, through a nostril of the subject and advancing the guide catheter to a location at or near the desired location and (D) advancing the device through the lumen of the guide catheter and to or through the desired location.

Further aspects, elements and advantages of the present invention will be understood by those of skill in the art upon reading of the detailed description set forth herebelow.

BRIEF DESCRIPTION OF THE DRAWINGS

FIG. 2B' is a transverse cross sectional view of a round wire before undergoing compression as illustrated in FIG. 2A.

FIG. 2B" is a transverse cross sectional view of the wire of FIG. 2B' after having undergone compression as illustrated in Figure 2B.

DETAILED DESCRIPTION

The following detailed description and the accompanying drawings are intended to describe some, but not necessarily all, examples or embodiments of the invention. The contents of this detailed description and the accompanying drawings do not limit the scope of the invention in any way.

Figure 1:
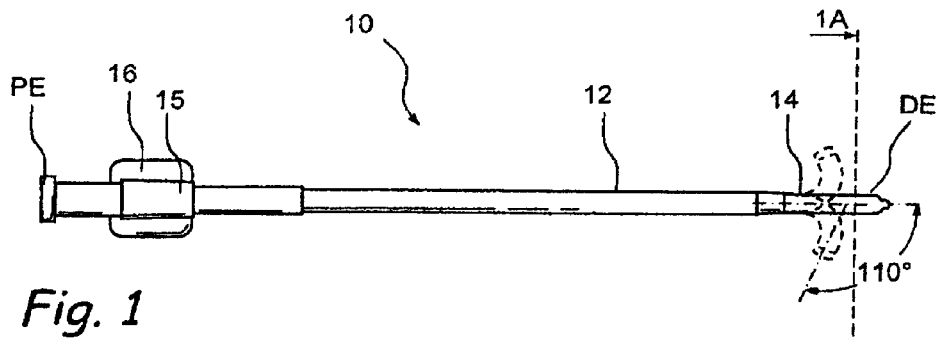
FIG. 1 is a side view of one embodiment of a malleable guide catheter of the present invention.
Figure 1A:
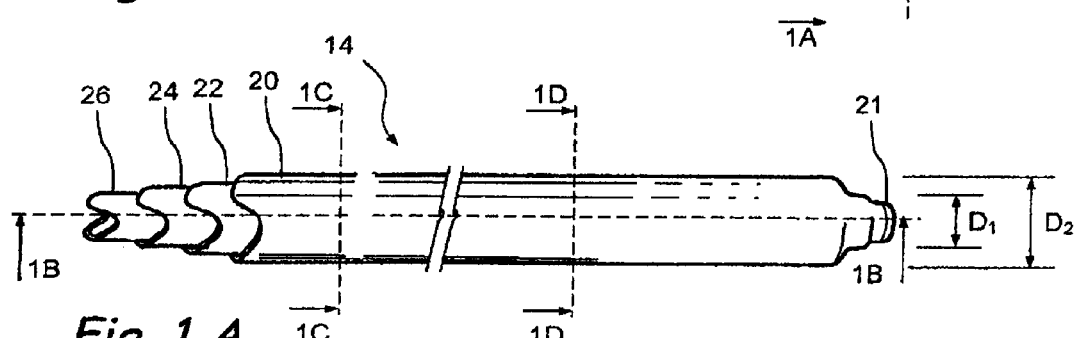
FIG. 1A is an enlarged, cut-away view of a distal portion of the guide catheter of FIG. 1.
Figure 1B:
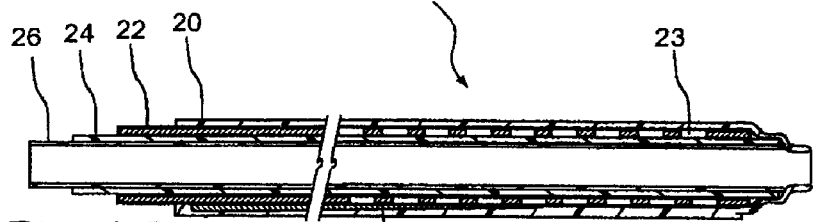
FIG. 1B is a longitudinal sectional view through line 1B-1B of Figure 1A.
Figures 1C, 1D:
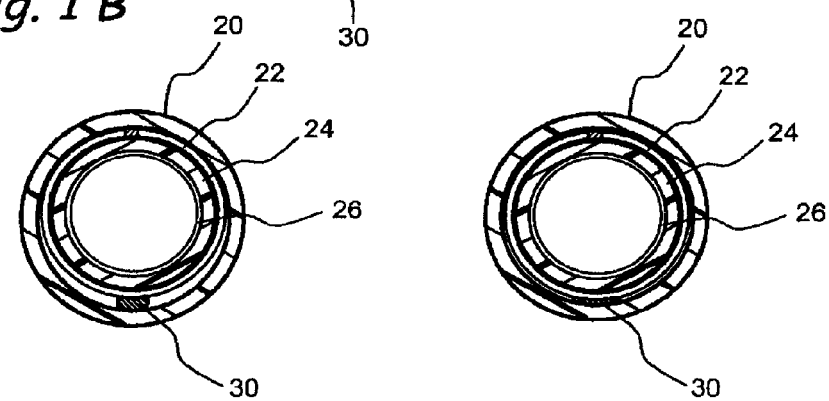
FIG. 1C is a transverse sectional view through line 1C-1C of Figure 1A.
FIG. 1D is a transverse sectional view through line 1D-1D of Figure 1A.

FIG. 1 shows one embodiment of a shapeable guide catheter 10 of the present invention. This guide catheter 10 comprises an elongate shaft 12 having a shapeable region 14 at its distal end DE and a Luer connector 15 having diametrically opposed wings 16 at its proximal end PE.

As may be appreciated from the showings of FIGS. 1A-1D, the elongate shaft 12 comprises a tubular member 22 having a helical cut 23 formed in a distal portion of the tubular member 22. This tubular member 22 may be formed of stainless steel hypotube, or any other suitable metal or plastic material. As explained more fully herein, the tubular member 22 is most flexible in the region of this helical cut 23 and, thus, the location of the helical cut 23 corresponds to the location of the shapeable region 14. A malleable shaping member 30, such as a segment of metal wire or other malleable material, is attached to the tubular member 22 in the region of the helical cut 23. An outer tubular jacket 20 is coaxially disposed outside of the tubular member 22 and an inner tubular member 24 is coaxially disposed inside of the tubular member 22. The outer tubular jacket 20 and inner tubular jacket 24 may be formed of polyurethane or other suitable plastic material and may be heat shrinkable as described below in connection with a method for manufacture of this catheter device 10. Optionally, a tubular liner 26 (e.g., thin walled polytetrafluoroethylene (PTFE) tubing may be disposed coaxially within the inner tubular jacket 24 to provide a smooth, lubricious inner luminal surface to facilitate advancement of guidewires and other devices through the inner lumen 27 of the shapeable guide catheter 10.

In operation, the user may grasp the distal end DE of the shapeable guide catheter 10 and manually bend or otherwise confirm the shapeable region 14 to a desired curvature or other shape. The malleable member 30 plastically deforms to accommodate such shaping of the shapeable regions and, thereafter, holds the shapeable region 14 in the desired curvature or other shape.

As will be explained more fully below, in some embodiments, the malleable member may be constructed and/or the width of the helical cut 23 may be varied, to provide regionalized variations in the flexibility or deformability of the shapeable region 14. Also, as described more fully below, the malleable member 30 may be more easily bendable in one plane than in another, thereby controlling the plane in which the shapeable region becomes curved. In such embodiments, the malleable member 30 may be oriented so as to be most easily bendable in a plane that is parallel to the plane of the diametrically opposed wings 16 on the proximal Luer hub. This allows the user to visually or tactilely discern the direction in which the distal portion of the catheter shaft 12 curves even when the distal portion of the catheter shaft 12 is inserted in the body of a subject.

FIGS. 2A-4C show further details of ways in which this embodiment of the shapeable guide catheter 10 may be constructed or manufactured.

Initially, as seen in FIG. 2A, a helical cut 23 is formed in a segment of stainless steel hypotube to create the tubular member 22. This helical cut 23 may be made by laser cutting or any other suitable technique. The width of the cut may be consistent over its entire length, as shown in the figures, or the cut 23 may be wider in some areas than others, thereby making the tubular member 22 more flexible in some areas than others. For manufacture of a shapeable guide catheter 10 sized for intranasal use in an adult subject, a segment of 9-11 gage stainless steel hypotube that is 10 to 25 cm in length may be used, the proximal end of the helical cut 23 may be located about 10 mm from the distal end of the hypotube and the distal end of the helical cut 23 may be located about 2 mm from the distal end of the hypotube. Although, in the embodiment shown in these drawings, a full thickness helical cut 23 is used, it will be appreciated that alternatively various other groove(s), aperture(s), cut(s) or other modifications may be made to weaken at least one region of the hypotube wall to render that region more flexible than the remainder of the hypotube.

After the helical cut has been made in the tubular member 22, the malleable shaping member 30 is welded, soldered or otherwise attached to the tubular member 22 in the region of the helical cut 23. In some embodiments, the malleable shaping member may be formed of round or flattened metal wire (e.g., annealed stainless steel wire). When a flattened wire is used, a segment of round wire may be pressed in a die as seen in FIG. 2B, or such round wire may be swaged, otherwise compressed or machined to a desired flattened shape. As indicated in FIGS. 2B' and 2B", when a round wire of diameter D is compressed, it will assume a flattened shape having a basal width B and a height H. In determining the optimal basal width B and a height H to be used, it may in some cases be desirable to determine what basal width B and a height H result in an area moment of inertia I that is equivalent to that of a round wire of a certain diameter. This may be determined, as follows:

For a round wire, the following equations apply:

$$I = \frac{\Pi D^4}{64}$$

$$A = \frac{\Pi D^2}{4}$$

$$D = \sqrt{\frac{4BH}{\Pi}}$$

For a flattened wire, the following equations apply:

$$I = \frac{BH^3}{12}$$

$$A = BH$$

$$B = \frac{12I}{H^3}$$

Wherein,
I=Area Moment of Inertia
A=Cross Sectional Area
D=Diameter of Round Wire
B=Width of Flattened Wire H=Height of Flattened Wire When manufacturing a shapeable guide catheter 10 suitable for intranasal use in adults, malleable shaping members 30 formed of round annealed stainless steel wire of either 0.030 inch or 0.035 inch diameter provide desirable properties (e.g., they are plastically deformable by hand but retain their shape with sufficient strength to avoid inadvertent changing of the shape as the catheter is being inserted and advanced through the intranasal anatomy.) The area moment of inertia I for such round wires are calculated to be as follows:

For 0.030 inch round wire, I=3.98E−08 in^4

For 0.035 inch round wire, I=7.37E−08 in^4

For a flattened wire to achieve an area moment of inertia I equivalent to that of either 0.030 inch 0.035 inch round wires, various other round wires having differing starting diameters may be compressed or otherwise flattened to different basal widths B and heights H, as shown in Table 1 below:

TABLE 1

| | For I Equivalent to 0.030 in. Round Wire | | | For I Equivalent to 0.035 in. Round Wire | | |
|---|---|---|---|---|---|---|
| Height (H) (in.) | Width (B) (in.) | Area Moment of Inertia (I) (in^4) | Original Wire (D) (in^4) | Width (B) (in.) | Area Moment of Inertia (I) (in^4) | Original Wire (D)(in.) |
| 0.010 | 0.477 | 3.98E−08 | 0.078 | 0.884 | 7.37E−08 | 0.106 |
| 0.011 | 0.358 | 3.98E−08 | 0.071 | 0.664 | 7.37E−08 | 0.096 |
| 0.012 | 0.276 | 3.98E−08 | 0.065 | 0.512 | 7.37E−08 | 0.088 |
| 0.013 | 0.217 | 3.98E−08 | 0.06 | 0.402 | 7.37E−08 | 0.082 |
| 0.014 | 0.174 | 3.98E−08 | 0.056 | 0.322 | 7.37E−08 | 0.076 |
| 0.015 | 0.141 | 3.98E−08 | 0.052 | 0.262 | 7.37E−08 | 0.071 |
| 0.016 | 0.116 | 3.98E−08 | 0.049 | 0.216 | 7.37E−08 | 0.066 |
| 0.017 | 0.097 | 3.98E−08 | 0.046 | 0.180 | 7.37E−08 | 0.062 |
| 0.018 | 0.082 | 3.98E−08 | 0.043 | 0.152 | 7.37E−08 | 0.059 |
| 0.019 | 0.070 | 3.98E−08 | 0.041 | 0.129 | 7.37E−08 | 0.056 |
| 0.020 | 0.060 | 3.98E−08 | 0.039 | 0.110 | 7.37E−08 | 0.053 |
| 0.021 | 0.052 | 3.98E−08 | 0.037 | 0.095 | 7.37E−08 | 0.051 |
| 0.022 | 0.045 | 3.98E−08 | 0.035 | 0.083 | 7.37E−08 | 0.048 |
| 0.023 | 0.039 | 3.98E−08 | 0.034 | 0.073 | 7.37E−08 | 0.046 |
| 0.024 | 0.035 | 3.98E−08 | 0.032 | 0.064 | 7.37E−08 | 0.044 |
| 0.025 | 0.031 | 3.98E−08 | 0.031 | 0.057 | 7.37E−08 | 0.042 |

In some embodiments, the round wire may be of tapered diameter such that the wire is largest in diameter at one end (e.g., the proximal end) and smallest in diameter at the other end (e.g., the distal end). Additionally, in some embodiments, as the wire is compressed, a transverse curvature may be created in the malleable shaping member 30 in conformity with the outer surface of the tubular member 22. Examples of these concepts are seen in FIGS. 1A-1C and 2C-2F, where the proximal end of the shaping member 30 has a height $H_1$ of 0.017 inch and a width $B_1$ of 0.070 inch, the longitudinal midpoint of the shaping member 30 has a H2 of 0.010 inch and a width B2 of 0.050 inch and the distal end of the shaping member 30 has a H3 of 0.005 inch and a width 63 of 0.020 inch.

Figure 2:
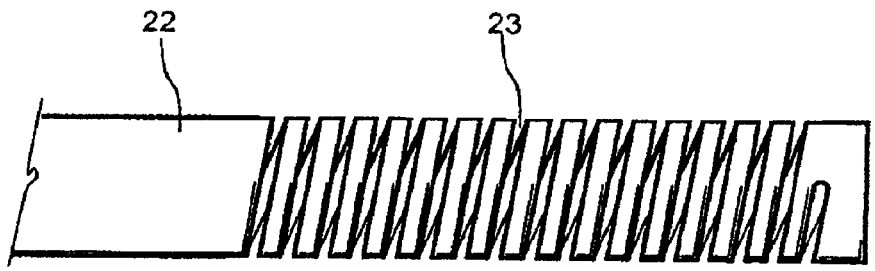
FIG. 2A is a side view of a helically cut tube component used in the manufacture of the malleable guide catheter of FIG. 1.
FIG. 2B is a schematic diagram showing an optional step in the manufacture of the malleable guide catheter of FIG. 1 wherein a shaping member component of the catheter is compressed from an initial round shape to a final non-round shape having flattened sides.
FIG. 2C is a side view of a helically cut tube component with one embodiment of a shaping member attached, as used in the manufacture of the malleable guide catheter of FIG. 1.
FIG. 2D is a partial view of the apparatus of FIG. 2C with the shaping member deformed to a curved shape.
FIG. 2E is a cross sectional view through line 2E-2E of FIG. 2D.
FIG. 2F is a cross sectional view through line 2F-2F of FIG. 2D.
FIG. 2G is a cross sectional view through line 2G-2G of FIG. 2D.
Figure 2:
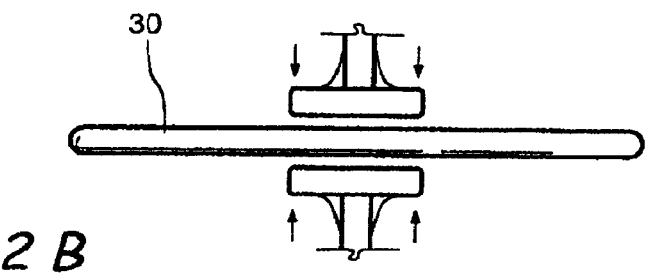
Figure 2:
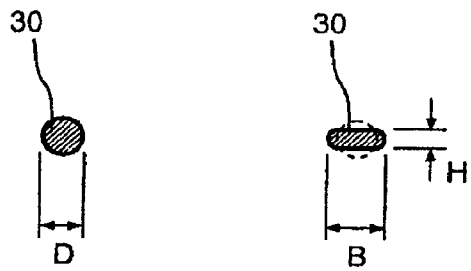
Figure 2:
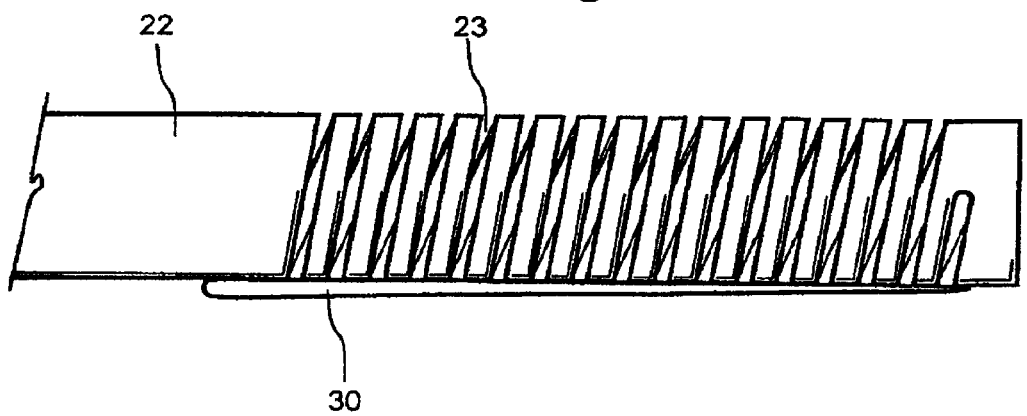
Figure 2:
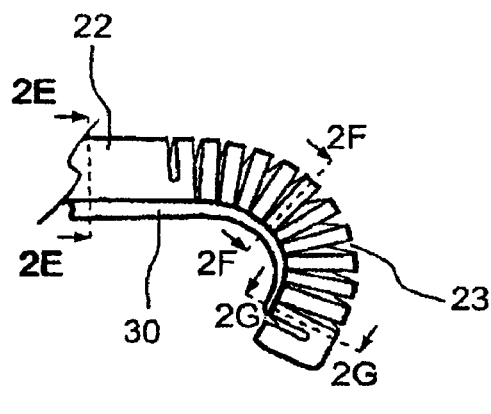
Figure 2:
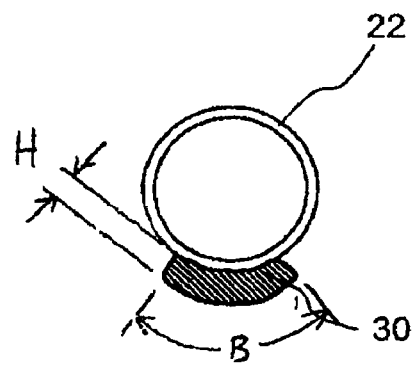
Figure 2:
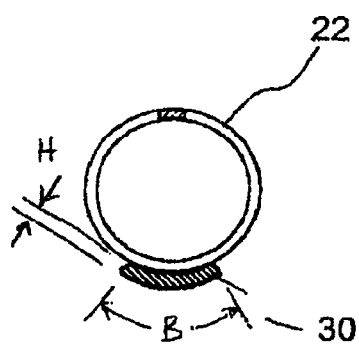
Figure 2:
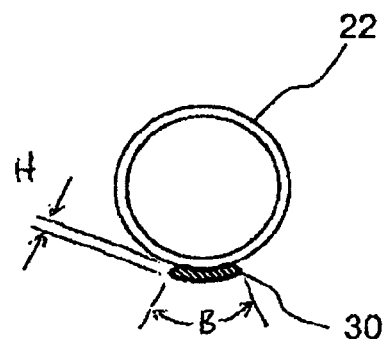

In the particular example shown in FIGS. 1-2G, a single malleable shaping member 30 is flattened, shaped to include a transverse curve and welded to the outer surface of the tubular member 22 in the area of the helical cut 23, as shown. However, it is to be appreciated that various other shapes and/or modes of attachment of the shaping member 30 may be employed, several non-limiting examples of such alternatives being a round wire attached to the outer surface of the tubular member 22, a flattened wire attached to the outer surface of the tubular member 22, a flattened/transversely curved wire attached to the outer surface of the tubular member 22, a flattened/transversely curved wire attached to the inner surface of the tubular member 22, or a flattened/transversely curved wire attached to the inner surface of the tubular member 22 and a second shaping member, such as a flattened/transversely curved wire, attached to the outer surface of the tubular member 22. Any permutations or combinations of these approaches, or various other approaches now specifically shown here, may be employed to provide the shapeable region 14 with the desired properties.

Figure 3A:
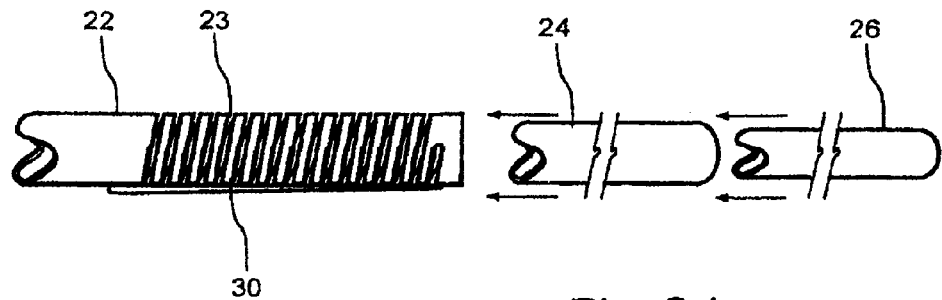
FIG. 3A shows a plastic inner tube being inserted into the lumen of the helically cut tube component after the shaping member has been attached and a plastic inner liner being inserted into the lumen of the plastic inner tube.
Figure 3B:
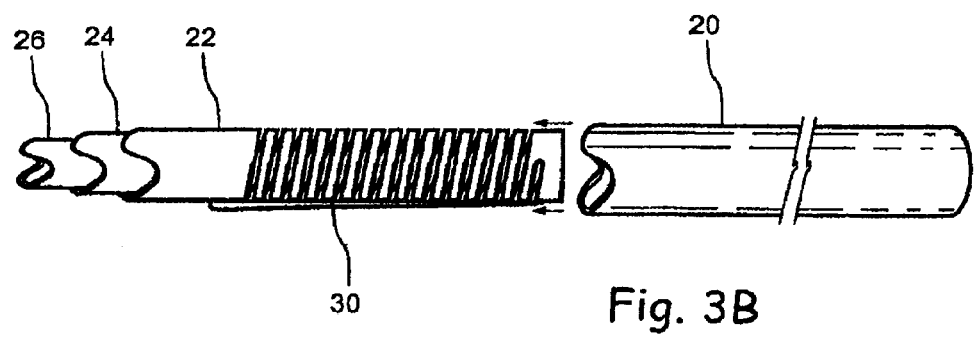
FIG. 3B shows a plastic outer jacket being advanced over the outer surface of the helically cut tube component, after the inner tube and inner liner have been inserted therein.
Figure 3C:
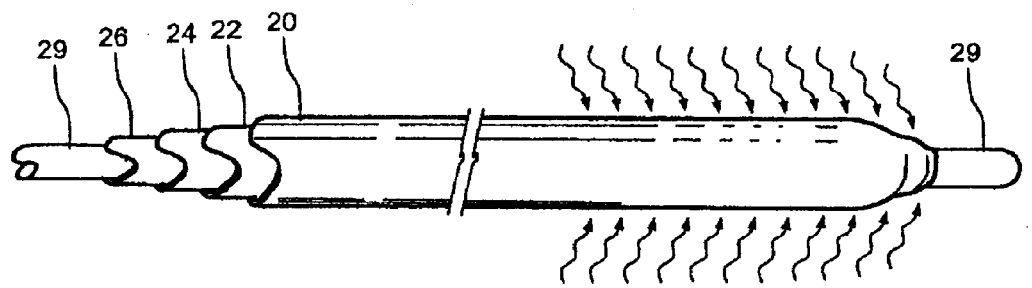
FIG. 3C shows a mandrel inserted through the lumen of the inner liner and heat being applied to heat-shrink the outer tube and to heat-fuse the outer tube, inner tube and inner liner in the region of the helical cut.

After the malleable shaping member 30 has been attached to the helically cut tubular member 22, the remainder of the guide catheter device 10 may be manufactured as shown in FIGS. 3A-3C or by any other suitable means. As seen in FIG. 3A, the tubular inner jacket 24 may be inserted into the lumen of the tubular member 22 and the optional inner liner 26 (if present) may be inserted into the lumen of the tubular inner jacket member 24. In an embodiment suitable for intranasal use in adult subjects, the tubular inner jacket 24 may comprise plastic tubing having an outer diameter of about 2.2 mm to about 3 mm and a wall thickness of about 0.1 mm to about 0.2 mm. The optional inner liner 26 may comprise a PTFE tube having an outer diameter of about 1.6 mm to about 2.8 mm and a wall thickness of about 0.05 mm.

Thereafter, as seen in FIG. 3B, the tubular outer jacket 20 may be advanced over the outer surface of the tubular member 22.

Thereafter, as seen in FIG. 3C, a mandrel 29 may be inserted through the innermost lumen of the device (e.g., through the lumen of the inner liner 26 (if present) or through the lumen of the tubular inner jacket 24 (if no inner liner is present). Heat (e.g., approximately 170 degrees C. to approximately 270 degrees C.) is then applied to heat shrink the outer jacket 20 onto the outer surface of the tubular member 22 and to cause the outer jacket 20, inner jacket 24 and inner liner 26 (if present) to heat fuse to one another through the helical cut 23. This ensures that the lumen of the device remains patent when it is shaped. In some embodiments, such as the embodiment shown in FIGS. 1 through 1D, 5 and 6, the plastic outer jacket 20, inner jacket 24 and inner liner 26 (if present) may extend distally some distance (e.g., 1 mm to 3 mm) beyond the distal end of the tubular member 22 and such protruding distal portions of these plastic components may be heat shrunk upon a reduced diameter mandrel 29, thereby providing a reduced diameter distal tip 21 on the distal end DE of the device 10. Such reduced diameter distal tip 21 may facilitate placement of the distal end DE of the device within a narrow opening or passage, such as within the ostium of a paranasal sinus.

Figure 4:
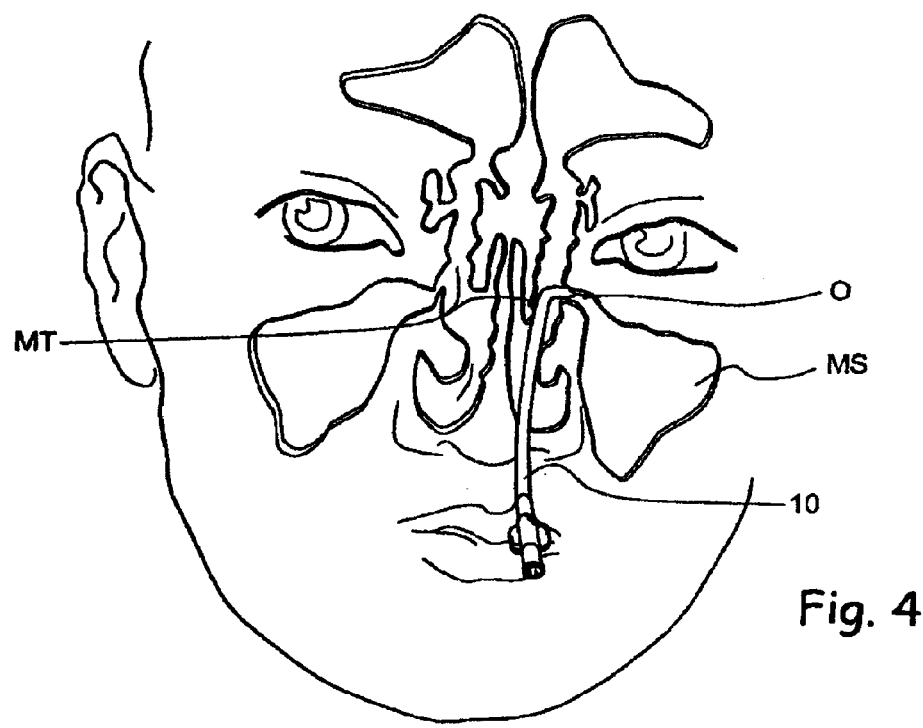
FIG. 4 is a diagram of a human patient with a malleable guide catheter of the present invention inserted trans-nasally and positioned adjacent to the ostium of the left maxillary sinus.
Figure 5:
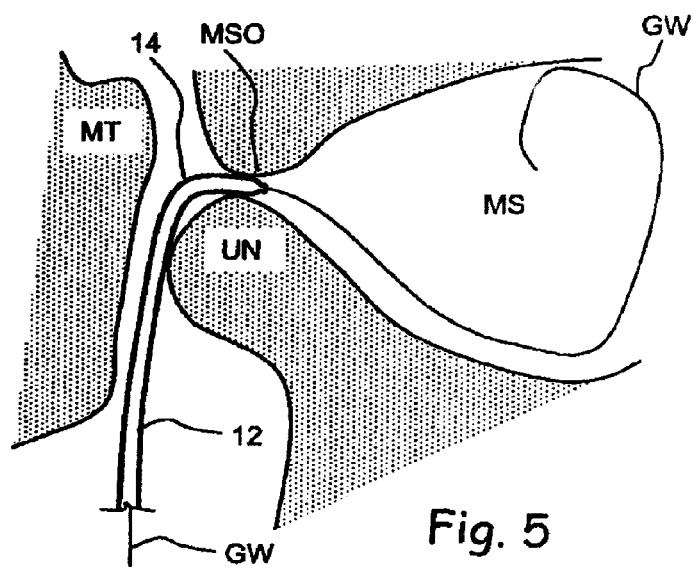
FIG. 5 is a schematic diagram showing a distal portion of a malleable guide catheter of the present invention shaped so as to extend around the intact uncinate process to a location adjacent to the ostium of the left maxillary sinus.

FIGS. 4 and 5 show examples of the manner in which a shapeable guide catheter 10 of the foregoing construction may be used to facilitate transnasal insertion of a guidewire GW into the maxillary sinus MS of a human subject. Initially, the operator may study preoperative X-rays or tomographic scans and/or may examine the anatomy around the ostium 0 of the maxillary sinus MS directly or endoscopically. After assessing the size, configuration and location of the maxillary sinus ostium MSO, as well as the surrounding anatomy, the operator will use his or her fingers (preferably while sterile) to bend the shapeable region 14 into a desired shape. Typically, the operator will select a shape that will facilitate advancement of the distal end DE of the guide catheter 10 to a position that is at or near a desired location. In this maxillary example, the "desired location" is the maxillary sinus ostium 0. Thus, to accomplish this, the operator may form the shapeable region 14 into a curve that will allows the distal end DE of the guide catheter 10 to be advanced through the middle meatus, around the uncinate process UN and into the hiatus semi-lunaris, resulting in placement of the reduced diameter distal tip 21 (or the distal end DE of the device 10 if no reduced diameter tip 21 is present) in front of or within the maxillary sinus ostium MSO. This will typically be done by advancing the guide catheter 10 while in a first rotational orientation to pass by the middle turbinate MT and then rotating the guide catheter 10 so as to "hook" the distal end DE around the uncinate process UN. In embodiments where the shapeable region 14 is curved in a plane that corresponds to the plane of the diametrically opposed wings 16 on the proximal Luer hub 15, the operator may feel or visualize the positioning of those wings 16 as an indicator of the current rotational orientation of the catheter 10. This will facilitate the "hooking" of the distal end DE around the intact uncinate process UN. In many procedures conducted using this guide catheter 10, the shapeable region 14 may be shaped to allow the distal end DE to reach the desired location with minimal or no surgical removal or damage to normal anatomical structures such as the uncinate process UN, middle turbinate MT or inferior turbinate. A particularly advantageous feature of the shapeable region located within about 1 cm to about 2 cm of its distal end is that the device may be inserted into the nasal cavity and then rotated and/or angled adjacent to the para-nasal sinus ostia with minimal or no damage to the normal anatomical structures.

Although there may be considerable anatomical variation among subjects, a curve in the shapeable region 14 of about 90 degrees to about 110 degrees may be suitable for accessing the maxillary ostia MSO of many subjects.

After the distal end of the guide catheter 10 has been successfully placed, a guidewire GW may be advanced through the guide catheter 10 and into or through the maxillary sinus ostium MSO, as shown in FIG. 5. Thereafter, catheter(s) or other apparatus may be advanced over the guidewire GW and through the guide catheter 10 to a position within the maxillary sinus ostium MSO and/or into the cavity of the maxillary sinus MS. Alternatively, in some applications, after the guidewire GW has been successfully placed to access the desired location, the guide catheter 10 may be removed and catheter(s) or other apparatus may be advanced over the guidewire GW alone, without the use of the guide catheter 10.

If for any reason the initial shape of the shapeable region 14 is not suitable, the operator may remove the guide catheter 10 from the nose, revise the shape of the shapeable region 14, and then once again attempt insertion and successful placement of the guide catheter 10 at or near the desired location. Also, since the shapeable region 14 of this guide catheter 10 is capable of being formed into various shapes, a single guide catheter 10 may be used for accessing multiple locations, such as the ostia of different sinuses and/or other openings in the nasopharynx. Examples of the multiple locations that may be accessed using this guide catheter 10 include but are not limited to the ostia or other natural or man made openings of the frontal, maxillary, sphenoid or ethmoid sinuses, the Eustachian tubes and/or the naso-lacrimal ducts, pathological lesions, tumors, abscesses, mucocoeles, polyps, cysts, fractures, or other disease-affected tissues. To allow this diversity of applications, the shapeable region 14 may be formable into curves of many shapes, including single plane radial curves ranging from 0 degrees (i.e., straight) to about 115 degrees or higher in some applications. For example, for some applications, the curve could be 170 degrees or more.

Optionally, for some embodiments of the invention, shaping tool(s) may be used to facilitate shaping of the shapeable region 14. For example, as those of skill in the art will appreciate, one or more shaping tools (e.g., jigs, templates, fixtures, patterns, or tools similar to a pipe benders) may be used to impart specific configuration(s) to the shapeable region 14. For example, the shaping tool may comprise a jigs, template, fixture, pattern or other apparatus into or onto which the shapeable region 14 is inserted or placed and deformed (e.g., bent) to a desired configuration in conformity with that shaping tool. In some embodiments, a mandrel may be included and such mandrel may be inserted into the lumen(s) of the device during the shaping process, thereby maintaining the desired cross-sectional shape of the lumen(s) and preventing localized indentation or crimping of the lumen wall or other portions of the device. For some applications a series of shaping tools having different configurations (e.g., curves of differing severity or differing radii of curvature) may be provided separately or may be positioned on or incorporated into a common housing (e.g., a plurality of different shaping fixtures positioned on or in a common housing such as a tray or other suitable housing structure).

Figure 6A:
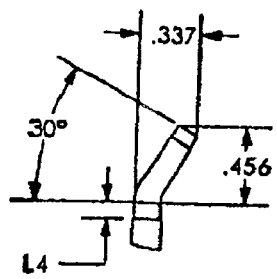
FIG. 6A shows a distal portion of a malleable guide catheter of the present invention wherein the shapeable region has been shaped to a configuration having a 30 degree curve suitable for trans-nasally accessing the ostia of a sphenoid paranasal sinuses.
Figure 6B:
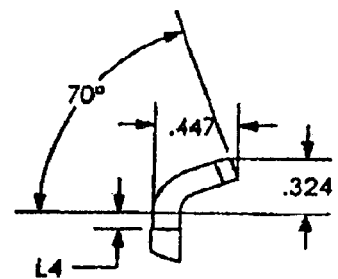
FIG. 6B shows a distal portion of a malleable guide catheter of the present invention wherein the shapeable region has been shaped to a configuration having a 70 degree curve suitable for trans-nasally accessing the ostia of a frontal paranasal sinuses.
Figure 6C:
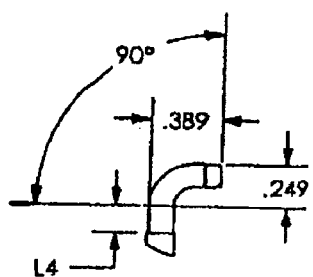
FIG. 6C shows a distal portion of a malleable guide catheter of the present invention wherein the shapeable region has been shaped to a configuration having a 90 degree curve suitable for accessing the ostia of maxillary paranasal sinus.
Figure 6D:
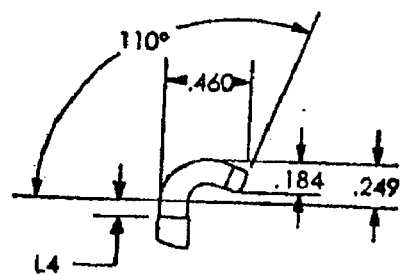
FIG. 6D shows a distal portion of a malleable guide catheter of the present invention wherein the shapeable region has been shaped to a configuration having a 110 degree curve suitable for accessing the ostia of a maxillary paranasal sinuses.

Irrespective of whether the shaping of the shapeable region 14 is carried out by hand or with the use of shaping tool(s), it may be desirable for the shapeable region 14 to be alternately configurable in shapes that are the same or substantially similar to those of the paranasal sinus guide catheters described in parent application Ser. No. 11/150, 847, now U.S. Pat. No. 7,803,150, issued on Sep. 28, 2010, which is expressly incorporated herein by reference. FIGS. 6A-6D of this application show several specific shapes that may be imparted to the shapeable region 14 to facilitate advancement and positioning of the distal end of the guide catheter device within or adjacent to/in alignment with the ostia of different paranasal sinuses. These specific shapes have curves of 30 degrees (FIG. 6A), 70 degrees (FIG. 6B), 90 degrees (FIG. 6C) and 110 degrees (FIG. 6D). The configuration having the 30 degree curve is typically useable for accessing the ostia of sphenoid sinuses or in some cases a 0 degree distal end shape is used for sphenoid sinuses. The configuration having the 70 degree curve is typically useable for accessing the ostia of frontal sinuses. The configuration having the 90 degree curve is typically useable for accessing the ostia of maxillary sinuses and in some cases frontal sinuses. The configuration having the 110 degree curve is typically useable for accessing the ostia of maxillary sinuses without requiring surgical removal or mitigation of the uncinate process. Each of these configurations shown in FIGS. 6A-6D have a transverse dimension or envelope that is small enough to allow the distal end of the guide catheter device to be inserted transnasally and advanced to the desired sinus ostium without requiring removal or surgical alteration of existing, normal anatomical structures within the nose.

Figure 7:
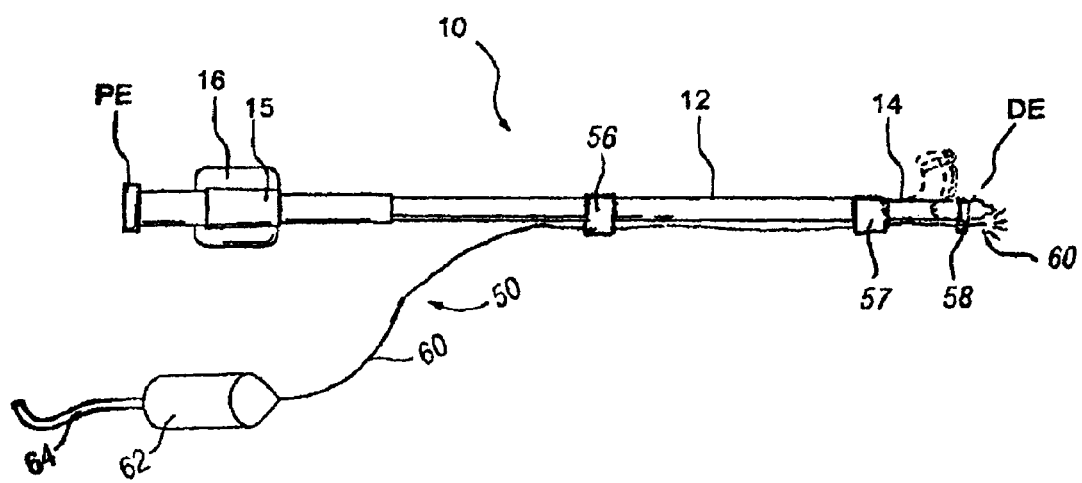
FIG. 7 is a side view of a malleable guide catheter of the present invention with an optional endoscopic system.

FIG. 7 shows the above-described guide catheter device 10 with an optional flexible endoscope system 50 that may be attached to or integrated with any guide catheter of this invention such that the guide catheter device may be used in conjunction with the endoscope system 50. This endoscope system 50 comprises a flexible endoscope 60, such as a fiber optic scope, that is attached to the shaft 12b of the guide catheter device 10b by way of connectors 56, 57, 58 such as clips, bands, snap-in grooves, etc. In some embodiments, the connectors 56, 57, 58 may be constructed to allow the endoscope 60 to be longitudinally advanced and retracted relative to the shaft of the guide catheter 10. The endoscope 60 is connected to a camera 62 and the camera 62 is connectable by way of camera cable 64 to a monitor on which an image received through the endoscope 60 may be displayed. Each endoscope 60 has a particular field of view. In this system, the vantage point of the endoscope 60 may be changed by changing the configuration of the shapeable region 14, thus bringing different anatomical structures and/or anatomical areas within the endoscope's field of view. Also, in embodiments where the endoscope 60 is advanceable, the degree of curvature of the shapeable region 14 may be changed to guide the advancement of the endoscope as desired. For example, if it is desired to cause the endoscope to advance through—the ostium of a paranasal sinus and into the sinus cavity, the operator may position the distal end DE of the guide catheter 10 near the ostium, visualize the ostium with the scope, and then guide the endoscope 60 into the ostium as desired. Also, in some applications, such as when it is desired to pass a guidewire or other device through the frontal outflow tract and into a frontal sinus, the operator may be faced with confusing anatomy, such as the presence of one or more false or blind openings in addition to the actual opening through which the guidewire or device is intended to pass. In such instances, the optional endoscope 60 may be used to assist the operator in serially or systematically probing or identifying each available opening, thereby facilitating identification of the correct opening and simplifying passage of the guidewire or device into the correct passage. Examples of endoscopes that may be used in this system include those described in U.S. patent application Ser. No. 11/803,695, entitled "Endoscopic Methods And Devices For Transnasal Procedures," filed May 14, 2007, now U.S. Pat. No. 9,554,691, issued Jan. 31, 2017; U.S. patent application Ser. No. 11/647,530, entitled "Endoscopic Methods and Devices for Transnasal Procedures," filed Dec. 27, 2006, published as U.S. Pub. No. 2007/0167682 on Jul. 19, 2007; U.S. patent application Ser. No. 11/725,151, entitled "Endoscopic Methods and Devices for Transnasal Procedures," filed Mar. 15, 2007, now U.S. Pat. No. 9,089,258, issued on Jul. 28, 2015, and U.S. Provisional Patent Application No. 60/844,874, entitled "Endoscopic Methods and Devices for Transnasal Procedures," filed Sep. 15, 2006.

The invention has been described hereabove with reference to certain examples or embodiments of the invention only. Various additions, deletions, alterations and modifications may be made to these examples and embodiments without departing from the intended spirit and scope of the invention. For example, any element or attribute of one embodiment or example may be incorporated into or used with another embodiment or example, unless otherwise indicated or unless doing so would render the embodiment or example unsuitable for its intended use. Also, where the steps of a method or procedure are referred to or listed in a specific order, the order of such steps may be changed unless otherwise specified or unless doing so would render the method or procedure unsuitable for its intended use. All reasonable additions, deletions, modifications and alterations are to be considered equivalents of the described examples and embodiments and are to be included within the scope of the following claims.

What is claim is:

1. A method for dilating an opening in a head of a human or animal subject with a shapeable guide member, wherein the shapeable guide member includes a shapeable region having a malleable member and a tubular member, the method comprising:
    (a) bending the malleable member of the shapeable region to a desired shape to facilitate advancement of a distal end of the guide member to a desired location, wherein the malleable member is attached to the tubular member, wherein the shapeable region is located closer to a distal end of the guide member than to a proximal end of the guide member, wherein the malleable member of the shapeable region substantially retains the desired shape after bending and holds the shapeable region in the desired shape, wherein the act of bending is performed by a human operator;
    (b) inserting the guide member, distal end first, into a head of the subject to position the distal end of the guide member at or near the opening in the head of the subject;
    (c) advancing a balloon along the guide member to position the balloon within the opening in the head of the subject; and
    (d) expanding the balloon within the opening in the head of the subject to thereby dilate the opening.

2. The method of claim 1, wherein the opening in the head of the subject comprises a paranasal sinus opening.

3. The method of claim 1, wherein the opening in the head of the subject comprises a Eustachian tube.

4. The method of claim 1, wherein the act of expanding the balloon comprises remodeling a tissue forming the opening.

5. The method of claim 4, wherein the act of remodeling the tissue comprises breaking or remodeling bone forming the opening.

6. The method of claim 5, wherein the act of remodeling the tissue comprises breaking bone forming the opening.

7. The method of claim 1, further comprising deflating the balloon, wherein the opening remains dilated after deflating the balloon.

8. The method of claim 1, wherein the malleable member is configured to be more easily bendable in one plane than in another plane and the method further comprises discerning a direction of the desired curve of the shapeable region when the desired curve is inserted into the head of the subject.

9. A method for dilating an opening in a head of a human or animal subject with a shapeable guide member, wherein the shapeable guide member includes a shapeable region having a malleable member, the method comprising:
    (a) bending the malleable member of the shapeable region to a desired shape to facilitate advancement of a distal end of the guide member to a desired location, wherein the malleable member of the shapeable region substantially retains the desired shape after bending and holds the shapeable region in the desired shape;
    (b) inserting the guide member into a head of the subject to position the distal end of the guide member at or near the opening in the head of the subject, wherein the opening is positioned between a first cavity and a second cavity, and wherein the opening has a smaller diameter than each of the first and second cavities;
    (c) positioning a balloon within the opening in the head of the subject between the first and second cavities; and
    (d) expanding the balloon within the opening in the head of the subject to thereby dilate the opening by remodeling the opening with the expanded balloon.

10. A method for dilating an opening in a head of a human or animal subject with a shapeable guide member, wherein the shapeable guide member includes a shapeable region having a malleable member, the method comprising:
  (a) bending the malleable member of the shapeable region to a desired curve to facilitate advancement of a distal end of the guide member to a desired location, wherein the malleable member of the shapeable region substantially retains the desired curve after bending and holds the shapeable region in the desired curve, wherein the desired curve is configured to enable positioning of the distal end of the guide member through the middle meatus of the subject, around the uncinate process of the subject, and into the hiatus semilunaris of the subject;
  (b) inserting the guide member into a head of the subject a first rotational orientation to pass the distal end of the guide member by the middle turbinate of the subject;
  (c) rotating the guide catheter to a second rotational orientation to hook the distal end of the guide member around the uncinate process of the subject and position the distal end of the guide member at or near the opening in the head of the subject;
  (d) advancing a balloon along the guide member to position the balloon within the opening in the head of the subject; and
  (e) expanding the balloon within the opening in the head of the subject to thereby dilate the opening.

* * * * *